United States Patent [19]

O'Connor

[11] Patent Number: 5,660,995
[45] Date of Patent: Aug. 26, 1997

[54] VETERINARY DRUG RESIDUE SURVEILLANCE METHOD

[75] Inventor: Michael O'Connor, Dublin, Ireland

[73] Assignee: Enfer Technology Ltd., Dublin, Ireland

[21] Appl. No.: 140,189

[22] PCT Filed: Mar. 1, 1993

[86] PCT No.: PCT/IE93/00007

§ 371 Date: Sep. 1, 1994

§ 102(e) Date: Sep. 1, 1994

[87] PCT Pub. No.: WO93/18408

PCT Pub. Date: Sep. 16, 1993

[30] Foreign Application Priority Data

Mar. 2, 1992 [IE] Ireland ................................. 920668

[51] Int. Cl.$^6$ .................. G01N 33/543; G01N 33/74
[52] U.S. Cl. .................. 435/7.93; 422/57; 435/962; 435/968; 436/518; 436/161; 436/172; 436/177; 436/825; 436/901
[58] Field of Search .................. 422/50, 52, 55, 422/57, 59, 62, 68.1, 70; 435/4, 7.1, 7.92, 7.93, 8.08, 962, 968, 971; 436/518, 524, 528, 161, 172, 174, 177, 816, 817, 825, 901, 905

[56] References Cited

U.S. PATENT DOCUMENTS 4,302,534  11/1981  Halmann et al. .................. 435/6
5,089,423  2/1992  Diamandis et al. .................. 436/518

OTHER PUBLICATIONS

Haasnoot et al., 1992. "Immuno-affinity chromatography in combination with an enzyme immunoassay for the determination of clenbuterol in poultry tissue", in Food Safety and Quality Assurance: Applications of Immunoassay Systems, Proc., 1st (Morgan et al., eds.) Elsevier Applied Science, London, UK. pp. 185–188.

McConnell et al., 1992. "Trenbolone and 19-nortestosterone residue analysis by immunoaffinity chromatography and high performance liquid chromatography and/or enzyme linked immunosorbent assay", in Food Safety and Quality Assurance: Applications of Immunoassay Systems, Proc., 1st (Morgan et al., eds.) Elsevier Applied Science, London, UK. pp. 245–250.

Berti et al., 1992. "Application of an enzyme immunoassay for the detection of the anabolic agents zeranol and 19-nortestosterone", in Food Safety and Quality Assurance: Applications of Immunoassay Systems, Proc., 1st (Morgan et al., eds.) Elsevier Applied Science, London, UK. pp. 207–214. Abstract only in Chemical Abstracts 117:732. Abstract No. 110238a.

Rapid Determination of Clenbuterol Residues in Urine by High Performance Liquid Chromatography with On–Line Automated Sample Processing Using Immunoaffinity Chromatography Hoosnaat et. al. (a) J. Chromatography 519 (1990) 323–335.

Enzyme Linked Immunosorbent Assay (ELISA): Theoretical and Practical Aspects Clark et al. Chapter 8 in "Enzyme Immunoassay" Ed. E.T. Magsib. 1987.

Residue Screening for the β–Agonists Clenbuterol, Solbutamol, and Cimaterol in Urine Using Enzyme Immunoassay . . . Meyer et al., J. Chromatography Biomedical Applications vol. 564 (1991) 551–556.

Determination of Clenbuterol in Bovine Tissue and Urine by Enzyme Immunoassay, Degand et al., J. Agric. Food Chem. 40, 70–75 (1992).

A Chemiluminescent Immunoassay for Zeranol and Its Metabolites, Jansen et al., J. Vet. Phyarmacol. Therap. 9, 101–108 (1986).

Food Additives and Contaminants, 1987, vol. 4, No. 2. 149–160, "Development of a sensitive microtitration plate . . . ".

W. Haasnoot et al., (b) "Determination of B–19–Nortestosterone and its Metabolite a–19–Nortestosterone in Biological Samples at the Sub Parts Per Billion Level . . . ", J. Chromatography, Biomedical Applications, vol. 489, No. 1, Apr. 7, 1989, Amsterdam, NL, pp. 157–171.

G. Degand et al., "Enzyme Immunoassay Screening Procedure for the Synthetic Anabolic Estrogens and Androgens Diethylstilbestrol, Nortestosterone, Methyltestosterone and Trenbolone in Bovine Urine", J. Chromatography, Biomedical Applications, vol. 564, 1991, Amsterdam, NL, pp. 551–556.

Patent Abstracts of Japan, vol. 7, No. 42, (P–177) (1198) Feb. 10, 1983.

S.N. Dixon et al., "The Anabolic Agent Zeranol.IV. The Determination of Zeranol Concentrations in the Edible Tissues of Cattle Implanted With Zeranol", J. Vet. Pharmacol. Therap., vol. 9, No. 1, 1986, pp. 94–100.

*Primary Examiner*—Paula K. Hutzell
*Assistant Examiner*—James L. Grun
*Attorney, Agent, or Firm*—Jacobson, Price, Holman & Stern, PLLC

[57] ABSTRACT

A method for the rapid detection of drug residues in livestock to allow quality certification, involves: taking a bile sample from livestock; cleaning the bile sample by passing the sample under vacuum through a porous silica immunoaffinity column having an immobilized antibody capable of binding the drug to be detected, washing the column free of impurities, and eluting any drug being bound to the column with a suitable solvent; and reacting the cleaned bile sample in a competitive immunometric assay utilizing a labelled antibody.

12 Claims, 4 Drawing Sheets

VETERINARY DRUG RESIDUE SURVEILLANCE METHOD

TECHNICAL FIELD

The present invention relates to a method for the rapid detection of veterinary drug residues in fresh meet or livestock and to a test kit for use in such a method.

BACKGROUND OF THE INVENTION

Field of the Invention

The illegal use of certain veterinary drugs has resulted in the development of a flourishing illicit market in these drugs which in turn presents a potential hazard for the consumer of product from treated animals.

Steers are traditionally used in the beef industry rather than bulls. Steers are less efficient, they grow 10% slower and have more fat and poorer conformation than bulls. Thus, beef producers used anabolic agents to increase growth before they were banned. However, since the EC ban in 1987, there have been varying allegations of illegal use of prohibited production enhancers in beef cattle. The possibility that a significant portion of beef might have residues of illegal growth enhancers could threaten consumption of beef.

Mandatory testing by national authorities of fresh meat, in compliance with EC Directives, covers a range of veterinary medicines and banned substances.

The extent of monitoring in compliance with EC Directives and 'on suspicion' is limited by the resources available to the authorities and thus will inevitably result in only a limited number of samples being monitored. In addition to this, the analytical methods used are laborious and costly. A further disadvantage of currently available commercial immunological assays is that they require at least one day for an end-point determination to be made. Thus the carcase being tested would have left the abattoir before the assay result is available.

An enzyme immunoassay screening for synthetic anabolic estrogens and androgens is known from Degand et al (Journal of Chromatography, 489 (1989) p235–234). The assay is an enzyme immunoassay involving either horseradish peroxidase or Beta-lactamase, which is conducted on bovine urine to detect diethylstilbestrol, nortestosterone, methyltestosterone and trenbolane. High-performance liquid chromatography following immunoaffinity pre-treatment to determine nortestosterone levels in biological samples is known from Haasnoot (Journal of Chromotography, 489 (1989) p157–171).

The analytical test protocol of the present invention represents a new approach to surveillance of fresh meat for drug residues. The approach has been to apply rapid clinical diagnostic techniques to veterinary drug residue analysis. This has the potential to permit large numbers of samples to be processed rapidly and much more cheaply than is currently the case. This approach permits the monitoring of large numbers of animals as they pass through abattoirs and offers the possibility of "Carcase Quality Certification (CQC)" before the carcase is allowed to enter the food chain.

The invention provides a series of semi-automated tests for a range of veterinary drugs, such as 'Angel Dust' (the Beta-Agonists-Clenbuterol, Salbutamol, Terbutaline etc), and for illegal hormonal growth promoters (Zeranol, Trenbolone, Stilbenes etc).

OBJECT OF THE INVENTION

The object of the invention is to provide a rapid method of detection of veterinary drug residues in fresh meat or livestock, with results being preferably available in a matter of hours. It is also an object that the detection method be cheap, reliable and user friendly.

SUMMARY OF THE INVENTION

According to the present invention there is provided a method for the rapid detection of drug residues in livestock comprising taking a body sample from the livestock, reacting the sample in an immunometric assay with a labelled antibody which is capable of reacting with the drug to be tested and determining the amount of labelled antibody bound to the sample, the antibody being labelled with a chromogenic label or a chemiluminescent label.

Preferably the sample is bile fluid. The antibody may be an anti-clenbuterol antibody or an anti-zeranol antibody.

The bile sample may be "cleaned" prior to immunometric assay to produce a sample containing only the analyte to be tested. Preferably, the bite sample is passed through an immuno affinity column having an immobilized antibody directed against the drug to be tested, the column is washed free of impurities and any drug bound to the column is eluted with a solvent. Clenbuterol may be eluted with 0.3% hydrochloric acid.

Preferably, the immunometric assay is a competitive assay in which a solid support (suitably a microtitration plate) is pre-coated with a carrier protein-drug conjugate, the "cleaned" bile sample and a rabbit anti-drug antibody are added to the solid support, allowed to react and the support washed, a labelled donkey anti-rabbit IgG antibody is added, allowed to react and then washed, a signal reagent is then added and the signal read. The label may be horseradish peroxidase, and the carrier protein may be thyroglobulin.

The immunometric assay may suitably employ the Amerlite (Trade Mark) enhanced luminescence system available from Amersham International.

The assay may be fully automated with the extraction of the samples on the immuno-affinity column and the enzyme linked immunosorbent assay being performed by primary and secondary robots respectively.

The invention also relates to a test-kit for the detection of drug residues in livestock which comprises a labelled anti-drug residue antibody.

Preferably the anti-drug residue antibody is an anti-clenbuterol antibody, or an anti-zeranol antibody.

The present invention has shown that the anti-clenbuterol antibody shows sufficient cross-reactivity to enable the system to identify other beta agonists such as salbutamol, terbutaline etc. This has the advantage that as it becomes apparent to those using the illegal substances that clenbuterol (the currently most used beta-agonist) can easily be identified and they switch to using other beta agonists these also can be identified.

DETAILED DESCRIPTION OF THE INVENTION

Sample Matrix

Figure 1:
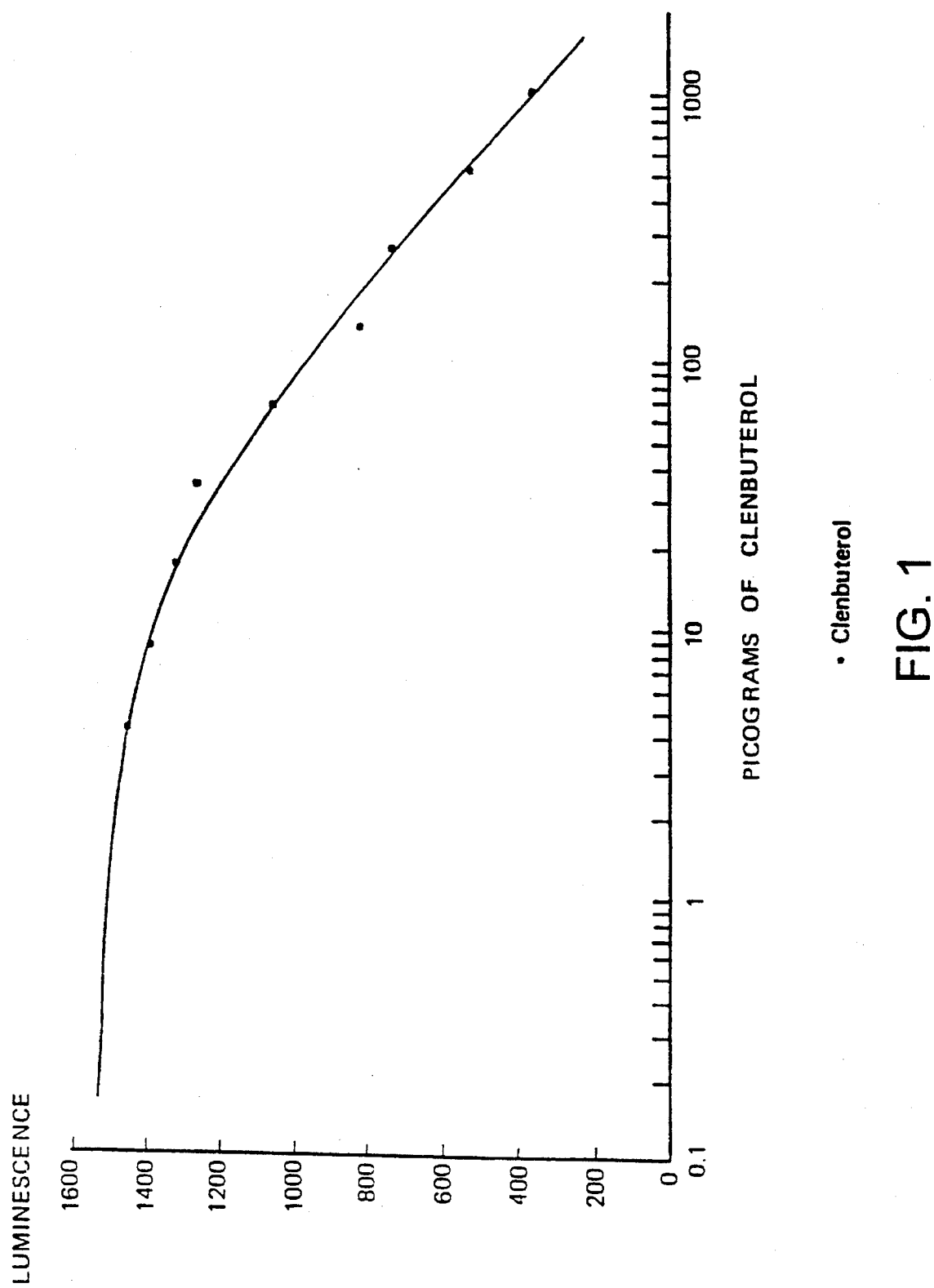
FIG. 1 is a calibration curve for clenbuterol.

Bile has been selected as the sample matrix of choice, as it is well established that the residues of the majority of veterinary drugs occur at a high concentration in this fluid. It is also readily obtainable and can be easily handled following collection.

Assay Development

The objective of the invention has been to develop a rapid surveillance test protocol involving the development of:

a) A rapid sample purification protocol, b) A rapid end point detection system a. Sample Purification

Due to the extremely sensitive nature of the detection system and its susceptibility to interference from impurities in the sample matrix, it is essential to prepare a clean extract containing only the analyte(s) (e.g. Beta-Agonists or hormonal growth promotors).

Utilising immunoaffinity columns through which the sample is allowed to percolate, immobilised antibodies react immunochemically with drugs present in the sample, absorbing them from the solution, the impurities passing through the column. The column is then washed with a buffer solution to remove any impurities remaining on the column, following this the drugs are eluted from the column with a specific solvent solution, to yield a clean sample extract which can be used in the end-point analysis.

The whole process is designed to permit the high degree of automation which will be necessary to permit the processing of large numbers of samples.

b. End Point Detection

This is an immunoassay which utilises an enhanced chemiluminescent end point. The test is conducted in 96 well microtitration plates, each of which permits about 40 samples (in duplicate) together with calibration standards, blanks and quality controls (QC), to be analyzed. The assay is formatted in the following manner using Clenbuterol as an example. A conjugate of Clenbuterol coupled to a carrier protein (Thyroglobulin) is absorbed on the surface of the wells of a microtitration plate. Into the wells are pipetted a known amount of rabbit anti-Clenbuterol antibody and Clenbuterol standard or sample extract, or QC, or Control (blank) extract. These are allowed to react immunochemically. Following this the contents of the wells are discarded and the wells washed with buffer solution. Into each well is pipetted a fixed amount of enzyme-labelled (Horse Radish Peroxidase) donkey anti-rabbit (IgG) antibody, this is allowed to react immunochemically. The microtitration plates are then emptied and washed with buffer solution, 'Enhanced Luminescent' reagent is then pipetted into each well and allowed to react for a fixed period of time before the chemiluminescence is determined. Using this approach and protocol the analytical system is able to provide a result of the Beta-Agonist residue status within about 2 hours of receiving the sample for analysis. In practical terms, allowing time for sample collection, processing and reporting of the result, 'carcase certification' can potentially be provided within about 4 hours of the animal being slaughtered.

The assay of the present invention thus provides a one and a half hour immunoassay of bile for beta agonists with a sensitivity of 0.3 parts per billion which is lower than current UK and expected EC maximum residue limits (MRL). This provides reliable, repeatable, fast assay results with a daily throughput of up to 1,000 samples per machine per day, and will allow the introduction of routine screening of all cattle slaughtered in meat factories for residues of beta agonists. Thus, carcases can be certified the same day by the veterinarian as free of residues before the carcase enters the human food chain and without disrupting the normal carcase processing and chilling routine in the factory. The fact that results are available within four hours of sample collection and the high throughput of the system on a daily basis are unique properties allowing all cattle slaughtered on a daily basis to be tested.

The system is such that it can rapidly adapt to screen for residues of new illegal drugs once antibodies have been generated against the illegal substance in question, and a suitable assay protocol is developed (<6 months in the case of a beta agonist test).

Target Assay Matrix:

Bile has been selected as the sample matrix of choice for assay. The residues of the majority of veterinary drugs occur at a high concentration in this fluid. It reflects concentrations of residues in the liver very accurately but has the advantage that it does not need to go through an initial tissue extraction step before preparation for assay. It is also readily obtainable and can be rapidly handled following collection. In some cases the concentration of residues of veterinary drugs in some edible tissues exceeds that in bile; however they are not readily extractable and may need extensive chemical manipulation prior to the final analysis.

Method of Collection of Bile Sample from Carcase

The main points to be considered in routine collection of bile samples are:

(i) Correlation of TB tag number of animal with carcass number and with sample collected.

(ii) Non-disruptive sample collection method from individual carcases: bile can be collected from each animal during evisceration of the animal.

(iii) Security of sample transfer to assay laboratory.

Assay Specification

Immunoaffinity Columns

Antibody: Rabbit and Sheep anti-clenbuterol antibody.
Immunoaffinity column matrix: Activated porous silica.
Immunoaffinity column container: Baker filtration columns.

Each column is filled with about 0.25 mls of porous silica to which the anti-clenbuterol antibody has been chemically bonded. Each column is capable of processing in excess of about 2ml of bile although only 1 ml of bile is processed at present. The chemical recovery of each column is better than 75% (77.8%±3.8%, n=9). The re-usability of the column is in excess of 20 times without any loss of performance.

Immunoassay

Assay standards: 0 to 500 pg (5) Quality Control Samples: Control Bile spiked at two concentrations either side of the target sensitivity of (0.5 ppb) which is the proposed MRL.
Assay Sensitivity; Standard curve (Bo)=approx. 0.2 ppb
Assay Limit of Detection (Bile): (mean bile Bo+3SD)=2 ppb Antibody Cross reactivity:

Clenbuterol 100%

Salbutamol 14%

Within (Intra) assay variation: at 10%

Between (Inter) assay variation: at 10–15%

Assay Protocols

Immunoaffinity Column

1. Pre condition the column with 3 ml of 0.3% Hydrochloric acid.

2. Wash the column with 3 ml of distilled water or phosphate buffered saline (PBS).

3. Apply the bile sample (1 ml to the column and allow to percolate through the column under gravity. (It is also possible to process 2 ml of bile and use the column to concentrate the analyte, this will increase the sensitivity of the assay). A vacuum can be applied to assist completion of this or any of the other steps.

4. Wash the column with distilled water (3 ml) or reverse osnosis grade water.

5. Elute the clenbuterol with 0.75 ml of 0.3% Hydrochloric acid.

6. Add 0.25 ml of 10×concentrate of PBS to the column eluate.

7. This extract is taken forward to the assay.

To reuse the immunaoffinity column for the purification of additional samples:

8. Wash the column with 1 ml of 50% ethanol/distilled water.

9. Wash the column with 1 ml of 0.34 hydrochloric acid.

10. Repeat procedure from step 1.

Enhanced Chemiluminescent Immunoassay

To the wells of a microtitration plate pre-coated with a Thyroglobulin—Clenbuterol conjugate, the following procedures are carried out:

1. Add 0.1 ml per well of extracted sample, blank QC or standard as appropriate.

2. Add 0.1 ml per well of rabbit anti-clenbuterol antibody diluted 1:50000 with PBS/Tween.

3. Shake for 40 minutes at 37° C., or at ambient temperature.

4. Wash 3 or 4 times with PBS/Tween 20 (0.05%).

5. Add 0.2 ml per well of Enzyme labelled Donkey anti-rabbit IgG antibody, diluted 1:5000 in PBS/Tween.

6. Shake for 30 minutes at 37° C., or at ambient temperature.

7. Wash 3 or 4 times with PBS/Tween 20 (0.05%).

8. Add 0.15 ml per well of Amerlite Signal Reagent and shake briefly.

9. Allow to stand for 3–10 minutes at ambient temperature then read the signal.

10. Data reduction test results printed out.

Sample Collection

The sample of bile is taken from the gall bladder attached to the liver while still in the abdomen of the carcase. The sample is taken using a pre-coded vacutainer (tamper-proof) which corresponds to the actual number of the carcase slaughtered on that day. The sample taken on a daily basis is related to the carcase number on a daily basis. The sample is taken at the evisceration area. The sample taken will be Situated at the evisceration stand and will remove the sample before removal of the pluck.

EXAMPLE 1

The determination of the Beta-Agonist clenbuterol residues in bile samples.

The following describes the procedure for the analysis of fresh bile samples obtained at the abattoir. The batch size is 40 which is equivalent to twice maximum capacity of the vacuum manifold currently used to process samples, the extracts from these samples (40) can be placed into one microtitration plate and analysed.

METHOD

Preparation of Clenbuterol Antibody

As clenbuterol will not stimulate an immune response when injected directly into an animal, it must first be converted into a form which will do so. This is facilitated by coupling Clenbuterol to a carrier protein (Bovine Serum Albumin—BSA,).

Clenbuten (20 mg) in a glass vial, is dissolved in dilute sulphuric acid and cooled in an ice bath. To this solution is added sodium nitrite solution, dropwise over a period of several minutes with stirring. After a further period of stirring, a solution containing the carrier protein (32 mg) is added, stirring is continued for a further 4 hours. The Clenbuterol—protein conjugate is then dialysed exhaustively against sodium bicarbonate buffer solution. Following the dialysis stage, any remaining uncoupled Clenbuterol and other constituents of the reaction mixture with the exception of the uncoupled protein are removed. (The presence of uncoupled protein in this solution is of no importance, as the primary objective is to generate an antibody to Clenbuterol. The antibodies generated to the carrier protein are unlikely to interfere with the assay—to date, there is no evidence to suggest that there is any interference of this nature, to the assay. If there were interference one can easily purify the anti-clenbuterol antibody and remove any antibodies to the carrier protein.)

The 'conjugate solution' is bottled and stored frozen until required for preparation of the immunising solution. It is assumed that all the clenbuterol has been conjugated to the carrier protein, but in practice this may not be the case.

Immunisation of Rabbits

The immunising solution is prepared immediately prior to use by thawing the frozen conjugate solution and allowing it to equilibrate to room temperature, mix gently. Pipette an appropriate volume equivalent to 1 mg of Clenbuterol—protein conjugate, per rabbit, into a glass vial, adjust the volume to 0.5 ml times the number of rabbits to be immunised, with PBS solution. To this solution add an appropriate volume (0.5 ml×the number of rabbits to be immunised) of Freunds Complete Adjuvant (Difco), emmulsify the mixture and store at 4° C. until required.

Each rabbit is immunised intra muscularly and subcutaneously with a total volume of 1 ml of the emmulsion. Booster injections using the same protocol are administered 3/4 weeks after the first immunisation. The animals are then left for a longer period (6/8 weeks) before the further boost injections. Tests bleeds are obtained both immediately prior to and about 10 days after each boost injection, the serum is separated and stored frozen at −20° C. until required for evaluation.

Samples

Numbered vacutainers containing the samples are placed in sequence in suitably labelled racks. Fresh samples must be allowed to equilibrate to room temperature before proceeding. (It is also possible to store samples frozen at −20° C., in which case the samples must be allowed to thaw and then thoroughly mixed prior to proceeding).

Extraction of the Clenbuterol from the Bile Samples a) Immunoaffinity column preparation:

Immunoaffinity columns (20) are placed into the 20 place vacuum manifold. The columns are washed in sequence with 0.3% Hydrochloric Acid (1 ml), the washes are discarded to waste. This is followed by washing each column with distilled water (1 ml) followed by PBS (3 ml), discarding the washes to waste. The columns are now ready to use for the extraction of bile samples, b) Treatment of bile samples:

The equilibrated bile samples (5 ml) are added to each column and allowed to percollate through the columns under gravity. When the samples have passed through the columns, the columns are then washed, under vacuum, with distilled waster (2×1 ml). Racks containing numbered sample tubes each containing 0.25 ml of a 10×concentrate of PBS are placed into the vacuum manifold. The columns are then eluted, under vacuum, into the respective samples tubes by pipetting 0.3% Hydrochloric Acid (0.75 ml) on to each column. The rack containing the extracted samples is then removed from the vacuum manifold and transferred to the immunoassay stage. The columns can now be regenerated to permit re-use.

c) Immunoaffinity Column Regeneration.

The columns are regenerated for further use by washing with distilled water (1 ml) followed by PBS (1 ml). The columns are now prepared for recycling as described above.

Immunoassay of Extracted Bile Samples

The tubes containing the extracted bile samples (1 ml), which have now been concentrated 5-fold, are placed in sequence into the carousel of the Denley Wellprep dispenser. The analyte-coated microtitration plate is washed with PBS/Tween 20 (0.3 ml×3) using a plate washer, the plates are inverted and tapped dry over paper towelling to remove excess liquid. The analyte coated microtitration plates used in the assay are coated with a Clenbuterol-protein conjugate (Clenbuterol-thyroglobulin), which is prepared in exactly the same manner as the immunogen, described above. The plate is then placed into the plate holder on the Wellprep. The dispensing programme is then initiated. Into pre-assigned wells of the microtitration plate is pipetted, in duplicate, an 0.1 ml aliquot of either the standard or the extracted sample. This is followed by the addition of 0.1 ml of the antibody diluted (1:50,000) in PBS. The plate is then removed from the Wellprep holder and transferred to a shaking incubator for 40 minutes at 37° C. Following this the plate is transferred to the plate washer and washed with PBS/Tween 20 (0.3 ml×3), the plate is then, removed from the plate washer, inverted, and tapped dry over paper towelling to remove excess liquid. Using a Denley Wellfill, 0.2 ml of Enzyme Labelled (Horse Radish Peroxidase-HRP) Donkey anti-rabbit IgG antibody diluted in PBS (1:5000) is dispensed into each well of the microtitration plate. The plate is then placed into the shaker incubator for a further period (30 minutes at 37° C). After the second incubation, the plate is placed in the plate washer and washed with PBS/Tween 20 (0.3 ml×3), removed from the plate washer, inverted and tapped dry over paper towelling to remove excess liquid. Using the Denley Wellfill to each well of the microtitration plate is added 0.15 ml of Amerlite Signal Reagent (Amersham International). The plate is covered with a plastic cover or film and allowed to stand for 6 minutes prior to transferring to a chemiluminescence plate feeder.

Data Transformation (computation of results).

Figure 2:
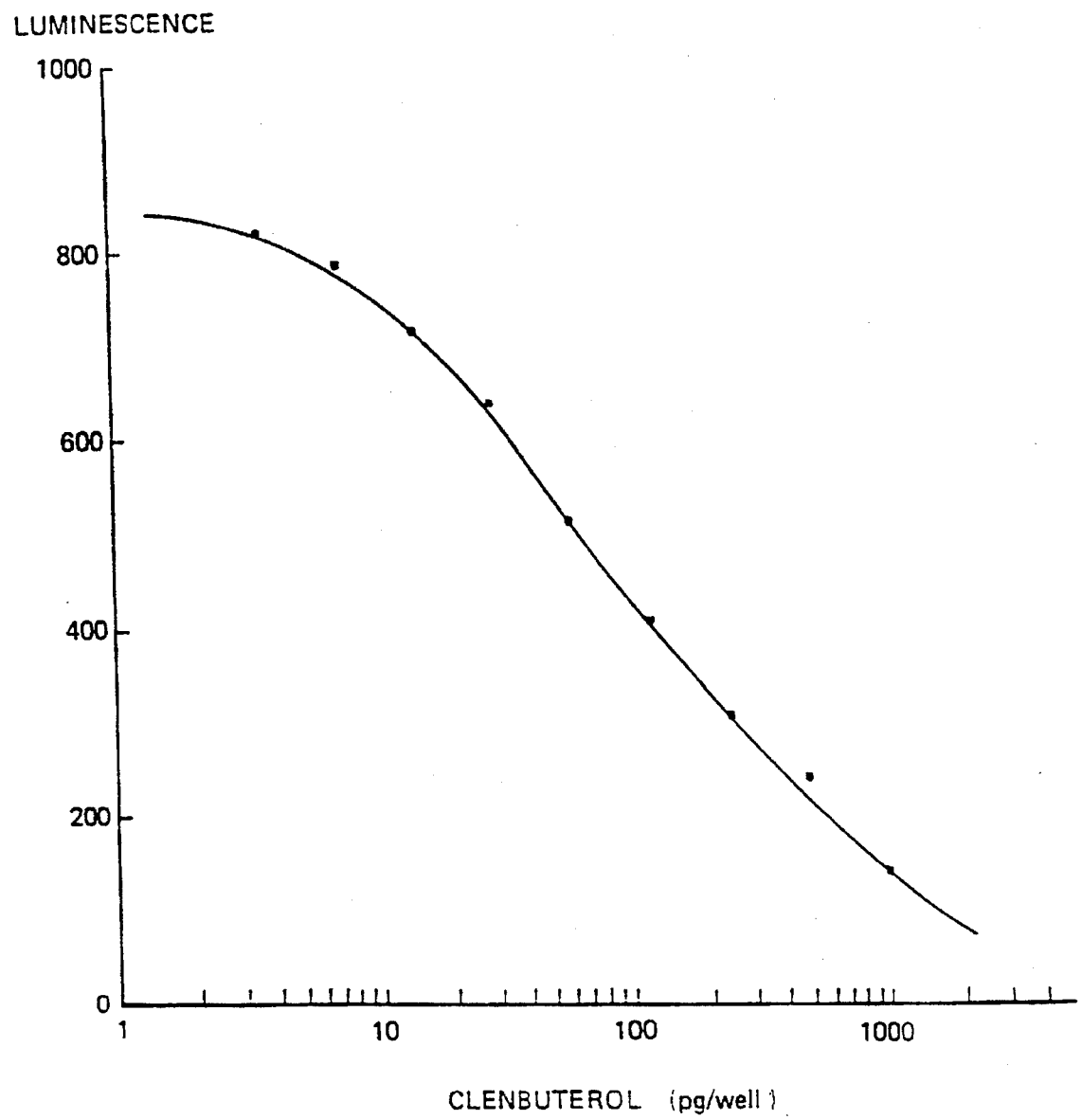
FIG. 2 is a clenbuterol standard curve.
Figure 3:
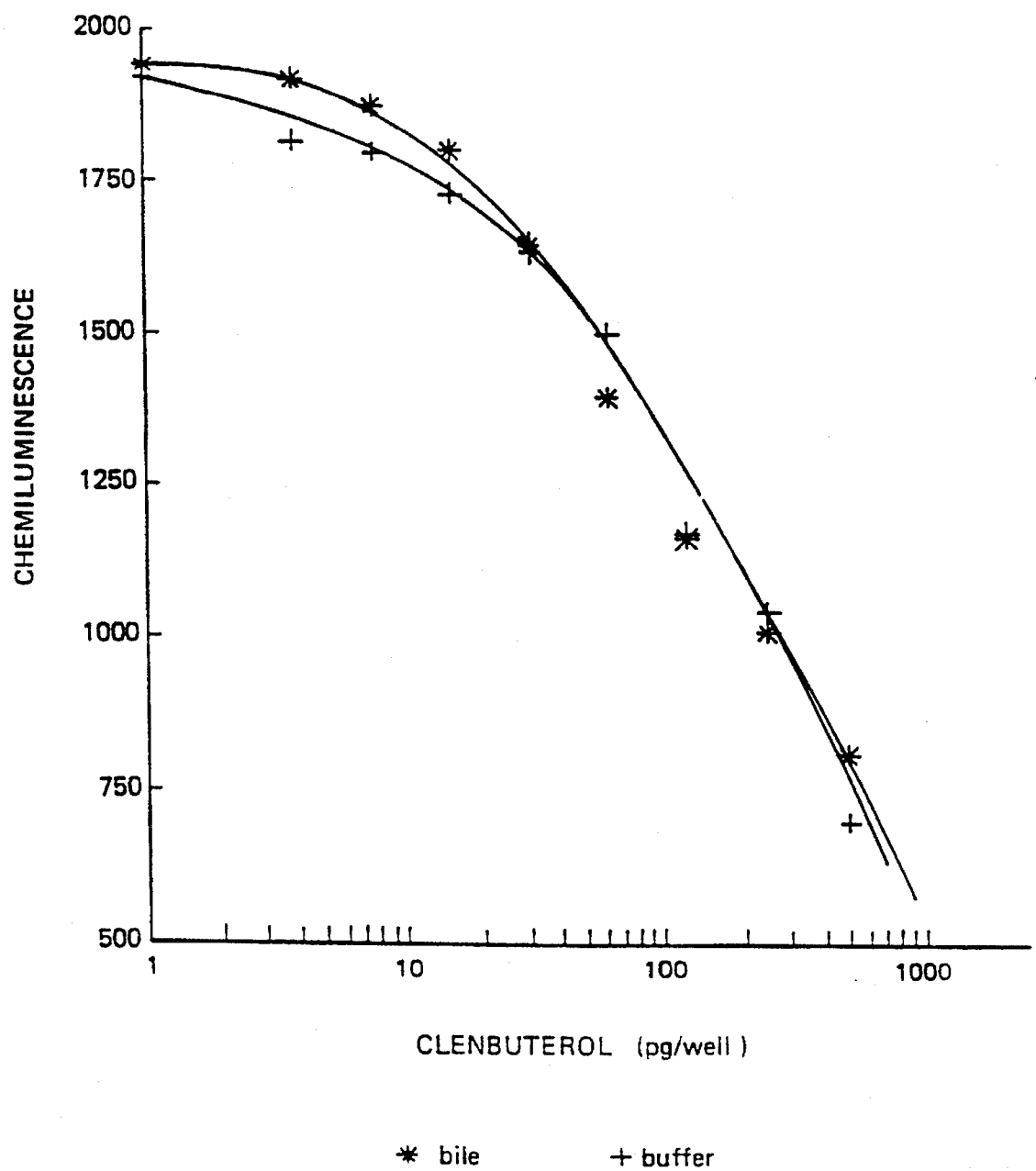
FIG. 3 is a standard calibration curve generated in the presence of an untreated bile extract.

The output from the plate reader is entered manually into a commercial software graphics package (Harvard Graphics) to produce a standard calibration curve. The mean luminescence values are then read-off this calibration curve. FIG. 1 shows a calibration curve for clenbuterol and FIG. 2 shows a clenbuterol standard curve which may be used to determine the amount of clenbuterol in the bile sample. FIG. 3 shows a standard calibration curve generated in the presence of a control, untreated bile extract which demonstrates that the effect of a bile extract on the calibration curve is minimal, with little or no effect on the calibration curve containing only extract buffer.

RESULTS

The results shown in Table I were obtained on fresh bile samples collected at two abattoirs. The first batch of samples was from animals which were claimed to have originated from a guaranteed source and had not been treated with any illegal medication. These animals can be considered to be control (untreated) animals and thus provided a baseline from which to deduce if a bile sample from an animal of unknown origin is likely to have been illegally treated. The mean of these values+3 Standard Deviations represents the Limit of Decision for the assay, values above this can be considered to be suspect and require further investigation. The confidence in this result is greater than 98%. The second batch of samples was from animals passing through an abattoir, the origin of these animals is unknown, they thus represent a 'field situation'.

TABLE I

| Batch 1 - Untreated animals - Control | | Batch 2 - Unknown origin - Abattoir | | | |
|---|---|---|---|---|---|
| Sample No. | Result - pg/ml | Sample No. | Result - pg/ml | Sample No. | Result - pg/ml |
| 46 | 30 | 36 | 54 | 78 | 500* |
| 47 | 25 | 37 | 55 | 101 | 360* |
| 48 | 30 | 38 | 47 | 102 | 1,500* |
| 49 | 33 | 39 | 75 | 103 | 39 |
| 50 | 30 | 40 | 60 | 104 | 75 |
| 51 | 30 | 41 | 57 | 105 | 450* |
| 52 | 10 | 42 | 45 | 107 | 600* |
| 53 | 0 | 43 | 33 | 109 | 400* |
| 54 | 30 | 44 | 30 | 111 | 450* |
| 66 | 0 | 45 | 36 | 112 | 1,200* |
| 67 | 0 | 46 | 60 | 113 | 1,200* |
| 68 | 0 | 47 | 27 | 114 | 170* |
| 69 | 5 | 48 | 48 | 115 | 380* |
| 70 | 7 | 49 | 75 | 116 | 60 |
| 71 | 0 | 50 | 79 | 117 | 900* |
| 72 | 15 | 51 | 75 | 123 | 21 |
| 73 | 150 | 52 | 70 | 124 | 1,500* |
| 74 | 0 | 53 | 65 | 125 | 8 |
| 75 | 18 | 54 | 50 | 126 | 36 |
| 77 | 45 | 55 | 64 | 127 | 480* |
| 78 | 48 | 56 | 1,500* | 128 | 20 |
| 79 | 0 | 57 | 250* | 129 | 39 |
| 80 | 10 | 58 | 300* | 130 | 29 |
| 81 | 48 | 59 | 600* | 131 | 0 |
| 82 | 10 | 60 | 540* | 132 | 0 |
| 83 | 0 | 61 | 600* | 133 | 23 |
| 84 | 0 | 62 | 500* | 134 | 5 |
| 85 | 0 | 63 | 380* | 135 | 0 |
| 86 | 0 | 64 | 500* | 136 | 3 |
| 87 | 0 | 65 | 400* | 137 | 18 |
| 88 | 0 | 66 | 300* | 138 | 3 |
| 89 | 0 | 67 | 600* | 139 | 0 |
| 90 | 30 | 68 | 500* | 140 | 0 |
| 91 | 23 | 69 | 380* | 141 | 45 |
| 92 | 9 | 70 | 90* | 142 | 25 |
| 93 | 0 | 71 | 450* | 176 | 1,200* |
| 94 | 5 | 72 | 450* | 177 | 210* |
| 96 | 36 | 73 | 600* | 178 | 1,500* |
| 97 | 87 | 74 | 200* | 179 | 140* |
| 98 | 0 | 75 | 1,500* | 180 | 120* |
| 99 | 46 | 76 | 900* | 181 | 500* |
| 100 | 5 | 77 | 380* | 182 | 120* |

Mean value 19.4048
Std Deviation 28.3700
Mean + 3SD = 104 pg/ml
*Denotes values in excess of the Limit of Decision (104 pg/ml)

EXAMPLE 2

Cross-reactivity with other Beta-Agonists

2. Antibodies

The Antibodies utilised in the immunoassay and the immunoaffinity columns were raised in both rabbits and sheep respectively, the immunogen being a protein/Clenbuterol conjugate. The general structure of the frequently used beta-agonists is given in Formula I, the meanings of the groups R1 to R4 being given in Table II.

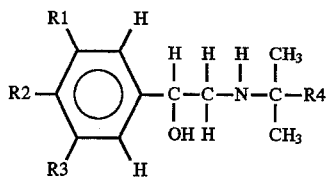

The cross reactivity of the rabbit antibody used in the immunoassay, determined at a clenbuterol concentration of 1 ng/ml is given in Table II.

TABLE II

| NAME | FUNCTIONAL GROUPS | | | | molwt | % CROSS REACTION |
|---|---|---|---|---|---|---|
| | R1 | R2 | R3 | R | | |
| Cimaterol | N≡C | NH$_2$ | H | H | 219.3 | 1.4 |
| Cimbuterol | N≡C | NH$_2$ | H | CH$_3$ | 233.3 | 6.7 |
| Clenbuterol | Cl | NH$_2$ | Cl | CH$_3$ | 277.2 | 100 |
| Mabuterol | CF$_3$ | NH$_2$ | Cl | CH$_3$ | 310.8 | 100 |
| Mapenterol | CF$_3$ | NH$_2$ | Cl | CH$_2$CH$_3$ | 324.8 | 55 |
| Salbutamol | H | OH | CH$_2$OH | CH$_3$ | 239.0 | 12.5 |
| Terbutaline | OH | H | OH | CH$_3$ | 225.0 | 8.3 |

The cross reactivity of the sheep antibody, used for the immunoaffinity columns, has been determined and found to be approximately:

| Clenbuterol | 100% |
|---|---|
| Salbutamol | 10.5% |
| Terbutaline | 6% |

The low cross-reactivity for salbutamol and terbutaline is not thought to be a problem as the columns are configured to provide high capacity for all these compounds. The enzyme labelled anitbody used for the detection of the "bound" antibody is raised in donkey against rabbit IgG. The IgG was isolated and conjugated to Horseradish Peroxidase.

EXAMPLE 3

Determination of Hormonal Growth Promotors

Figure 4:
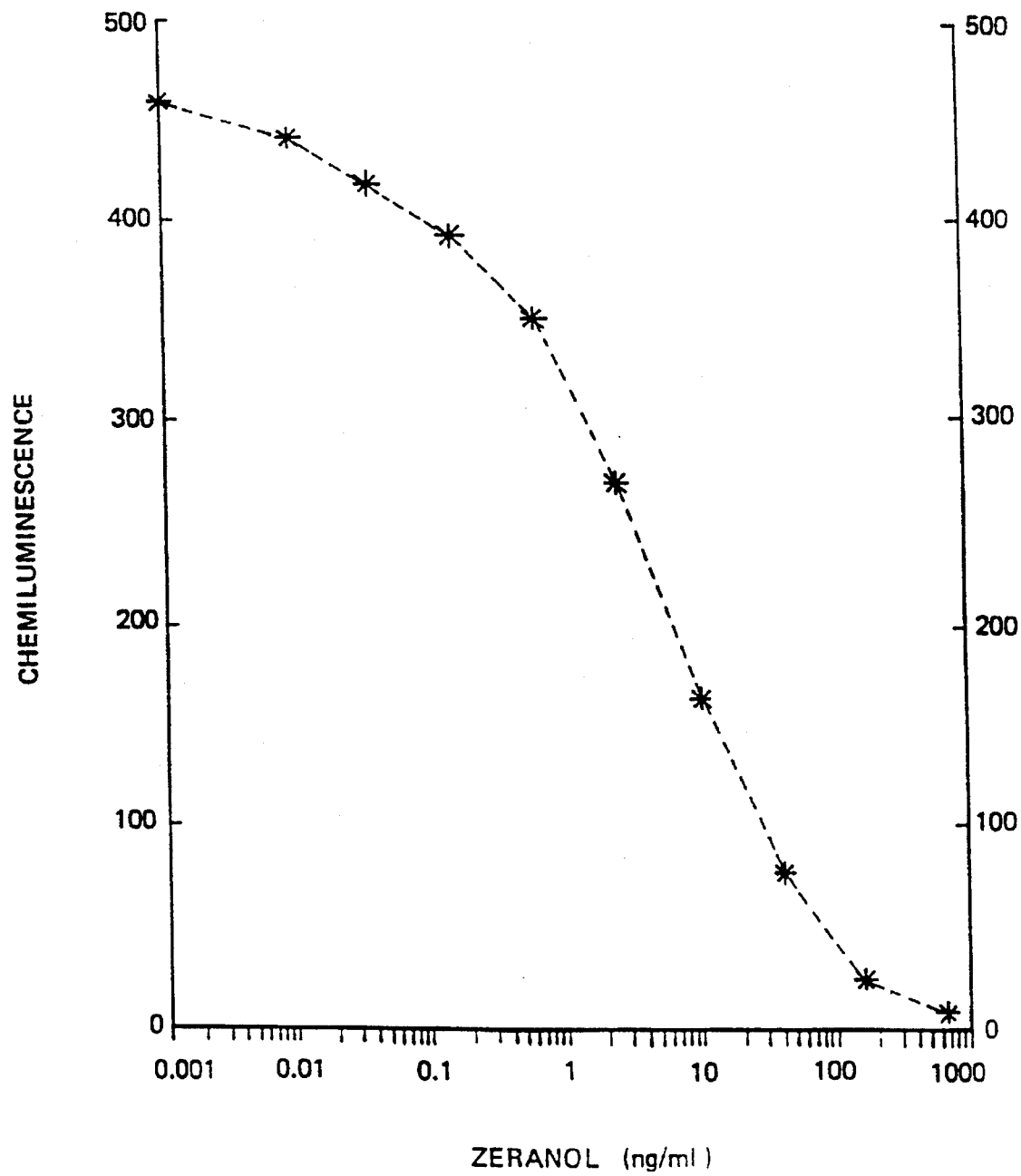
FIG. 4 is a standard calibration curve for zeranol.

The preparation of anti-zeranol antibodies was as described in Example 1 but using zeranol in place of clenbuterol and the assay protocol and computation of results is as described previously. FIG. 4 shows a standard calibration curve for zeranol from which the amount of zeranol in a bile sample can be determined.

Assay Sensitivity

The $B_o$ value for the assay buffer has been determined on 24 buffer samples analyzed in duplicate, in a single assay. The assay sensitivity is determined as the mean of the $B_o$-3 standard deviations (SD), the value obtained is 0.04 ng/ml.

Limit of Detection $B_{o\ sample}$ values for 324 control bile samples, obtained from untreated animals of all ages, sexes and sexual maturity etc., were analyzed in 18 clenbuterol assays. The value for the Limit of Detection is 0.055 ng/ml and is based on the means $B_{o\ sample}$ value+2 SD, the mean value+SD is 0.029± (2×0.013) ng/ml for all samples. A breakdown of the data according to animal type is as follows (ng/ml):

| | Steers | Cows | Heifers | Bulls | Total |
|---|---|---|---|---|---|
| Mean | 0.0296 | 0.0298 | 0.0281 | 0.0223 | 0.0290 |
| SD | 0.0120 | 0.0131 | 0.0126 | 0.0199 | 0.0127 |
| n | 144 | 76 | 93 | 11 | 324 |

Individual groups of animal do not differ statistically from either of the other groups, or the mean of all of the animals.

The Limit of Determination based on the minimum quantity of clenbuterol detectable with any statistical confidence was determined by spiking a 1l control bile sample. As the quantity of control bile was limited, the bile was initially spiked at 0.1 ng/ml and the sample analyzed in replicate. On the basis of the results obtained the concentration of clenbuterol in the bile was reduced to 0.05 ng/ml and the sample re-analyzed in replicate.

| 0.05 ng/ml Spike | 0.1 ng/ml Spike |
|---|---|
| Mean = 0.036 ng/ml | Mean = 0.089 ng/ml |
| SD = 0.092 | SD = 0.019 |
| Mean Recovery % = 72% | = 90% |

I claim:

1. A method for the rapid determination of the presence of a drug residue in a livestock animal wherein the drug is a β-agonist or hormonal growth-promoter comprising the steps of:
    a) taking a bile sample from the animal;
    b) cleaning the bile sample by (i) passing the sample under vacuum through a porous silica immunoaffinity column having immobilized thereon an antibody under conditions wherein the antibody specifically binds the drug residue, (ii) washing the column free of unbound sample, and (iii) eluting any drug residue bound to the column with a solvent, thereby providing a clean bile sample; and
    c) detecting any drug residue in the clean bile sample with a competitive immunometric assay.

2. The method of claim 1 wherein the drug is clenbuterol.

3. The method of claim 1 wherein the drug is zeranol.

4. The method of claim 1 wherein the competitive immunometric assay involves:
    pre-coating a solid support with a conjugate of the drug and a carrier protein to provide a drug-conjugate-coated solid support;
    reacting on the coated solid support the clean bile sample with an antibody from a first animal species, under conditions wherein the antibody specifically binds the drug coated on the solid support and any drug residue in the clean sample;
    washing the reacted solid support;
    contacting the washed reacted solid support with an enzyme-labeled anti-first species antibody raised in a second species of animal under conditions for specific antibody binding;
    washing the contacted solid support;
    adding a chromogenic or chemiluminescent enzyme substrate to the washed contacted solid support; and
    detecting a signal generated from reaction of enzyme label of the anti-first species antibody with the enzyme substrate, said signal indicative of drug residue present.

5. The method of 4 wherein the enzyme label is horseradish peroxidase.

6. The method of 4 wherein the carrier protein is thyroglobulin.

7. The method of claim 5 wherein the carrier protein is thyroglobulin.

8. The method of 4 wherein the first species of animal is a rabbit and the second species of animal is a donkey.

9. The method of claim 5 wherein the first species of animal is a rabbit and the second species of animal is a donkey.

10. The method of claim 6 wherein the first species of animal is a rabbit and the second species of animal is a donkey.

11. The method of claim 7 wherein the first species of animal is a rabbit and the second species of animal is a donkey.

12. The method of claim 1 wherein the cleaning and detecting steps are performed by robots.

* * * * *